United States Patent [19]

Matsuo et al.

[11] 4,351,587
[45] Sep. 28, 1982

[54] APPARATUS FOR POSITIONING EYEPIECE OF ENDOSCOPE

[75] Inventors: Kazumasa Matsuo, Tama; Tetsumaru Kubota, Hachioji, both of Japan

[73] Assignee: Olympus Optical Company, Ltd., Japan

[21] Appl. No.: 124,457

[22] Filed: Feb. 25, 1980

[30] Foreign Application Priority Data

May 3, 1979 [JP] Japan ................................ 54/25786
May 3, 1979 [JP] Japan ................................ 54/25787
May 3, 1979 [JP] Japan ................................ 54/25788

[51] Int. Cl.³ ............................................... G02B 7/04
[52] U.S. Cl. .................................... 350/255; 350/410
[58] Field of Search ..................... 350/19, 255, 410; 354/62, 63; 128/4, 6

[56] References Cited

FOREIGN PATENT DOCUMENTS 45-27677  9/1970  Japan .
47-44489 11/1972  Japan .
52-23977  5/1977  Japan .
52-20263  6/1977  Japan .

Primary Examiner—F. L. Evans
Attorney, Agent, or Firm—Ostrolenk, Faber, Gerb & Soffen

[57] ABSTRACT

An apparatus for positioning the eyepiece comprises a photographic positioning cam sleeve formed with a photographic positioning cam slot, and a dioptry adjusting cam sleeve formed with a dioptry adjusting cam slot. A dioptry adjusting pin is received in the cam slots and, as a photographing device is mounted on the endoscope, is driven by means of its engagement with the cam slots to position the eyepiece at a predetermined photographing position.

20 Claims, 35 Drawing Figures

APPARATUS FOR POSITIONING EYEPIECE OF ENDOSCOPE

BACKGROUND OF THE INVENTION

The invention relates to an apparatus for positioning eyepiece of endoscope, and more particularly, to such apparatus which is adapted to permit a picture of an object which has been previously observed to be taken by suitably mounting a photographing device such as camera on an eyepiece assembly.

In an endoscope employing a bundle of optical fibers for transmission of an image and which is used to enable an external observation of the inner wall of a cavity or channel such as a coeliac cavity, the eyepiece assembly of the endoscope includes an eyepiece which is disposed to be movable in the direction of the optical axis to permit an adjustment of the dioptric power of the eyepiece in accordance with the particular condition of the eyes of a viewer. When taking a picture of an image being observed, as by mounting a photographing device such as camera on the eyepiece assembly, the eyepiece is used as part of the objective lens assembly for taking the photograph.

Generally speaking, the position of the eyepiece where a dioptric power adequate for the eyes of a viewer is obtained is different from eyepiece position which should be used when taking a picture. If a good image is formed during the observation process, a sharply focused image cannot be obtained if a picture is taken with the eyepiece maintained in the same position. Consequently, when taking a picture, it is necessary that the eyepiece which has once been adjusted in position to provide an adequate dioptric power for observation purpose be moved to another position. An apparatus for positioning the eyepiece is used at this end. An apparatus is known in which the eyepiece is moved to a given photographing position as a photographing device is mounted on the eyepiece assembly of the endoscope, and a variety of such arrangements have been proposed previously.

By way of example, Japanese Patent Publication No. 44,489/1972 discloses an arrangement including a pin which is driven for sliding movement as a photographing device is mounted on the endoscope so that the eyepiece may be moved to a position where it is free from the influence of a dioptry adjusting cam. Also, Japanese Patent Publication No. 27,677/1970 discloses an arrangement including a cam sleeve which is angularly driven as a photographing device is mounted to move a dioptry adjusting pin to a location where it is free from the influence of a dioptry adjusting cam while permitting a movement of the eyepiece to a photographing position. Finally, Japanese Patent Publication No. 20,263/1977 and Japanese Utility Model Publication No. 23,977/1977 disclose an arrangement including a cam sleeve which is angularly driven as a photographing device is mounted to move a dioptry adjusting pin into cooperation with a photographic positioning cam which is mechanically associated with a dioptry adjusting cam so that an eyepiece integral with the dioptry adjusting pin can be moved to a photographing position.

However, the described arrangements in which the pin or the cam sleeve is either linearly or angularly driven to move the eyepiece beyond the reach of the dioptry adjusting cam are subject to a limitation that a photographing position for the eyepiece cannot be chosen which lies within the extent of the dioptry adjustment.

In the arrangement using the photographic positioning cam which is mechanically associated with the dioptry adjusting cam, the positioning of the eyepiece during a photographing operation is enabled only when the dioptry adjusting pin has moved past the end of the dioptry adjusting cam and bears against the photographing position cam. Hence, it follows that the cam sleeve must be angularly driven through a greater angle than that required for the adjustment of the dioptry in order to move the eyepiece to its photographing position. Thus an angular movement through an increased angle is required as the photographing device is mounted, which makes operation of the photographing device unnecessarily cumbersome.

An endoscope is known which permits a photographing device to be mounted thereon through a mere fitting engagement rather than requiring an angular movement, and is commonly known as an endoscope of the hard type. However, endoscopes of the hard type are generally not provided with a dioptry adjusting mechanism. If some provision is made to permit an adjustment of the dioptry, the positioning of the eyepiece must be performed manually during a photographing operation, again resulting in a cumbersome operation and unreliability.

SUMMARY OF THE INVENTION

In view of the foregoing, it is an object of the invention to provide an apparatus for positioning the eyepiece of an endoscope, which apparatus includes a photographic positioning cam sleeve having a photographic positioning cam slot which is utilized in order to position an eyepiece at its photographing position. A dioptry adjusting cam sleeve having a dioptry adjusting cam slot is provided, and a dioptry adjusting pin which is formed integrally with the eyepiece is held between the two cam slots, so that during a photographing operation, the eyepiece is brought to a given photographing position within the extent of adjustment of the dioptry through a reduced stroke as a photographing device is mounted on the endoscope.

It is another object of the invention to provide an apparatus for positioning the eyepiece of an endoscope, which apparatus includes a photographic positioning cam sleeve having a photographic positioning cam slot which is utilized to position an eyepiece at a photographing position, and which further includes a dioptry adjusting cam sleeve having a dioptry adjusting cam slot is used to locate the eyepiece at a position where a desired dioptry is obtained, and there is provided interlocking means responsive to a mounting of a photographing device to be driven thereby for angularly moving the photographic positioning cam sleeve. The photographic positioning cam sleeve is annularly driven as the photographing device is fitted into the eyepiece assembly of the endoscope, with a dioptry adjusting pin integral with the eyepiece being held between the cam slots to bring the eyepiece to a given photographing position within the extent of adjustment of the dioptry.

It is a further object of the invention to provide an apparatus for positioning the eyepiece of an endoscope, which apparatus includes a photographic positioning cam sleeve having a cam slot which is utilized to position an eyepiece at its photographing position, and which further includes a dioptry adjusting cam sleeve having a cam slot for adjusting the dioptry of the eyepiece. A photographing sleeve is integrally connected to the photographic positioning cam sleeve through an interconnecting resilient means, and interlocking means for causing an angular movement of the photographing sleeve is provided, the eyepiece being brought to a given photographing position within the extent of adjustment of the dioptry in response to a mounting, by fitting, of a photographing device onto the eyepiece assembly of the endoscope and independently of the stroke through which the photographing device is moved to mount it on the endoscope.

In accordance with the invention, it is unnecessary to connect the photographic positioning cam with the dioptry adjusting cam, so that the overall size of the cam slots can be reduced, resulting in the advantage that the angle required for the angular movement of the photographic positioning cam sleeve upon mounting a photographing device is one-half that required in the prior art arrangement. In this manner, the mounting of the photographing device is greatly facilitated.

The eyepiece can be brought to a photographing position which is within the extent of adjustment of the dioptry.

An operation of the dioptry adjusting ring while the eyepiece is positioned at its photographing position in response to a mounting of the photographing device, does not cause a displacement of the eyepiece, thus avoiding any interference with a photographing operation.

When the photographing device is dismounted after the completion of a photographing operation, the eyepiece is automatically returned to the position which it had prior to the photographing operation and where the dioptry is adjusted, thus permitting continued observation without re-adjustment of the dioptry.

Also, in accordance with the invention, the photographing device can be mounted on the eyepiece assembly of the endoscope by fitting, dispensing with a rotation as required in the prior art, thus facilitating a mounting of the photographing device.

Since there is no need to form any special groove or projection on or in the photographing device in order to permit its mechanical association with other parts, a variety of photographing devices having strokes of different lengths for their fitting engagement with the eyepiece assembly can be used.

Furthermore, as the photographing device is mounted, any interconnected member moves through a reduced stroke, so that the eyepiece assembly of the endoscope need not be provided with a large opening, but may be sealed against water by rubber rings or rubber gaskets.

DESCRIPTION OF PREFERRED EMBODIMENTS

Figure 1:
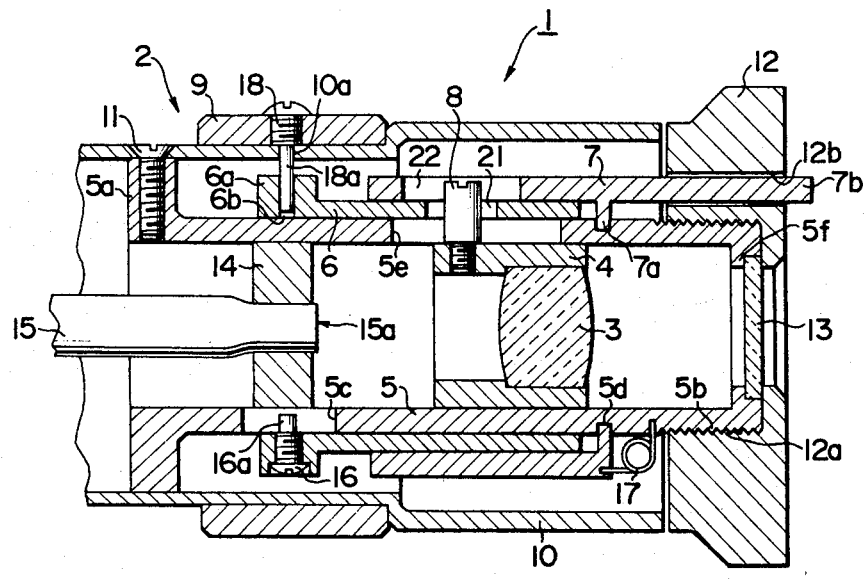
FIG. 1 is a longitudinal section of an apparatus for positioning the eyepiece of an endoscope according to one embodiment of the invention.

Referring to FIG. 1, there is shown an apparatus for positioning the eyepiece of an endoscope according to one embodiment of the invention. The apparatus 1 is adapted to be assembled into an eyepiece assembly 2 of an endoscope, and essentially comprises a movable sleeve 4 carrying an eyepiece or eyepiece lens 3, a fixed sleeve 5 in which the movable sleeve 4 is closely but slidably and rotatably fitted, a dioptry adjusting cam sleeve 6 which tightly fits around the exterior of the fixed sleeve 5 and which is slidable parallel to the optical axis, a photographic positioning cam sleeve 7 which tightly fits around the exterior of the dioptry adjusting cam sleeve 6 and which is rotatable about the optical axis, a dioptry adjusting pin 8 fixedly mounted on the external surface of the movable sleeve 4, and a dioptry adjusting ring 9 for causing the dioptry adjusting cam sleeve 6 to slide parallel to the optical axis.

The fixed sleeve 5 comprises a hollow cylindrical body having a mounting flange 5a on its free end, or the left-hand thereof, as viewed in FIG. 1. The flange 5a is disposed against a cylindrical frame 10 fixedly connected with the body of the proximate end of an endoscope, which frame 10 represents an operating assembly thereof, and is secured therein by a set screw 11. The opposite end or the right-hand end, as viewed in FIG. 1, of the fixed sleeve 5 is externally formed with threads 5b, which are threadably engaged by threads 12a formed in the inner surface of a short, cylindrical frame 12 which is to receive an eyepiece and photographing device thereon, whereby the frame 12 can be secured to the fixed sleeve 5. The frame 12 has its rear portion of an increased diameter. At its rear end, the fixed sleeve 5 is formed with a radially inwardly extending ledge 5f, and a cover glass 13 is held between the ledge 5f and the frame 12. Toward its front end, the fixed sleeve 5 is formed with an axially extending, elongate guide slot 5c which is disposed in the lower wall thereof. A set screw 16 is threadably engaged with the dioptry adjusting cam sleeve 6 and is integrally formed with a pin 16a which extends into the slot 5c. Toward its rear end, the external surface of the fixed sleeve 5 is formed with a guide groove 5d which extends in the circumferential direction and which loosely receives at least one guide pawl 7a formed on the photographic positioning cam sleeve 7. Intermediate its length, the upper wall of the fixed sleeve 5 is formed with a relief slot 5e which has a length greater than the stroke through which the dioptry adjusting pin 8 moves. In this manner, the pin 8 extends through the slot 5e. The emitting end of a bundle of optical fibers 15, which form an image guide, is secured to the front portion of the fixed sleeve 5 by means of a fixing member 14 so that the emitting end face 15a thereof is disposed in opposing relationship with the eyepiece 3.

Figure 2:
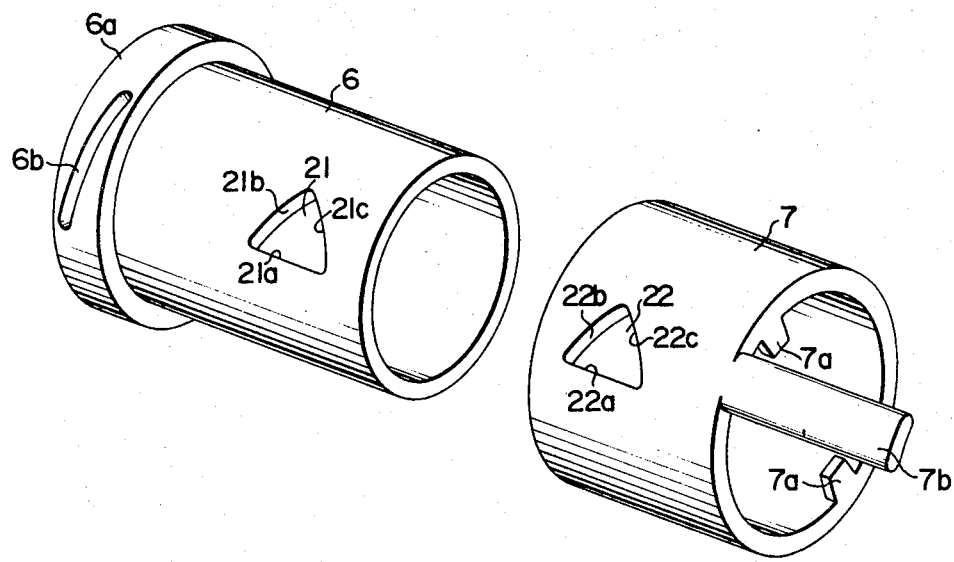
FIG. 2 is a perspective view of a dioptry adjusting cam sleeve and a photographic positioning cam sleeve used in the apparatus of FIG. 1.

The dioptry adjusting cam sleeve 6 comprises a hollow cylinder having an outwardly directed flange 6a on its front end, which is formed with a cam slot 6b (see FIG. 2) disposed at an angle with respect to the circumferential direction for converting a rotating movement of the dioptry adjusting ring 9 into a reciprocating movement of the dioptry adjusting cam sleeve 6. The flange 6a is also provided with the guide pin 16a mentioned above. The cooperation of the guide pin 16a and the guide slot 5c permits the dioptry adjusting cam sleeve 6 to move only axially. As shown in FIG. 2, the upper wall of the dioptry adjusting cam sleeve 6 is formed with a dioptry adjusting cam slot 21 substantially in the form of an equilateral triangle and having one side which extends parallel to the optical axis. The dioptry adjusting pin 8 extends through the cam slot 21. It will be noted that the cam slot 21 has a cam surface 21a extending parallel to the optical axis, and a pair of cam surfaces 21b and 21c which extend from the opposite ends of the cam surface 21a.

Figure 3:
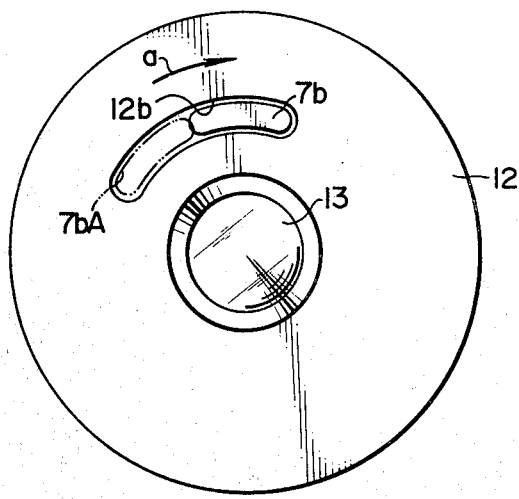
FIG. 3 is a front view of the eyepiece assembly of an endoscope on which the apparatus shown in FIG. 1 is mounted.

The photographic positioning cam sleeve 7 is again in the form of a hollow cylinder having a pair of diametrically opposite guide pawls 7a which extend radially inward from the rear end thereof and having an interlocking arm 7b extending in the direction of the optical axis from the rear end face of the cam sleeve 7 in its upper region. The guide pawls 7a loosely fit in the guide groove 5d. The cooperation between the guide pawls 7a and the guide groove 5d permits only an angular movement of the cam sleeve 7 in the circumferential direction. The interlocking arm 7b also extends through an arcuate slot 12b (see FIG. 3) formed in the frame 12 and projects beyond the rear end of the frame 12. Referring to FIG. 3, as a photographing device is mounted, the arm 7b is moved from its position shown in solid line to position 7bA shown in phantom line against the resilience of a coiled return spring 17 (see FIG. 1) to be described later. As shown in FIG. 2, toward its front end, the upper wall of the photographic positioning cam sleeve 7 is formed with a positioning cam slot 22 substantially in the form of an equilateral triangle into which the upper portion of the dioptry adjusting pin 8 extends. As shown, the cam slot 22 is in conformity to the cam slot 21, and includes a cam surface 22a which extends in the direction of the optical axis and a pair of cam surfaces 22b and 22c which extend from the opposite ends of the cam surface 22a. A coiled tension spring 17 (see FIG. 1) is disposed between the photographic positioning cam sleeve 7 and the fixed sleeve 5 to urge the photographic positioning cam sleeve 7 to rotate clockwise as indicated by an arrow a shown in FIG. 3. However, the resulting rotation is limited by the abutment of the cam surface 22a of the cam slot 22 against the dioptry adjusting pin 8 which in turn bears against the cam surfaces 21b, 21c of the cam slot 21.

Referring to FIG. 1, it will be noted that the dioptry adjusting ring 9 is tightly fitted around the frame 10, and a set screw 18 radially extends through the ring 9 and carries an integral guide pin 18a which cooperates with an elongate guide slot 10a formed to extend circumferentially in the frame 10 to permit angular movement of the ring 9 in the circumferential direction, but to prevent movement thereof in the direction of the optical axis. The inner end of the guide pin 18a extends into the cam slot 6b formed in the cam sleeve 6, whereby angular movement of the dioptry adjusting ring 9 causes the dioptry adjusting cam sleeve 6 to slide parallel to the optical axis.

The operation of the apparatus 1 will now be described. When the dioptry is adjusted in order to permit an observation of the interior of a coeliac cavity, the dioptry adjusting ring 9 is turned circumferentially to cause a forward or rearward movement of the dioptry adjusting cam sleeve 6 axially by cooperation of the guide pin 18a and the cam slot 6b. The dioptry adjusting pin 8 is located at the apex of the cam slot 21 formed in the dioptry adjusting cam sleeve 6 where it is urged against the both cam surfaces 21b, 21c by means of the axially extending cam surface 22a of the cam slot 22 formed in the cam sleeve 7, which is urged in the circumferential direction, as indicated by an arrow $a_O$ in FIG. 4(A). The pin 8 is now driven axially as the cam slot 21 moves parallel to the optical axis, while being constrained by the cam surface 22a of the cam sleeve 7. Consequently, the eyepiece 3 supported by the movable sleeve 4 on which the dioptry adjusting pin 8 is fixedly mounted also moves parallel to the optical axis. In this manner, a viewer can adjust the ring 9 until a sharp image is formed, thus achieving an adjustment of the dioptry in accordance with his eyes.

When a picture of the image being observed is to be taken, a photographing device (not shown) is mounted on the frame 12. As it is mounted, a groove or a detent tab formed with the photographing device causes the interlocking arm 7b to rotate together with its integral photographic positioning cam sleeve 7 in the opposite direction from that indicated by the arrow a and against the resilience of the return spring 17 until the position 7bA shown in phantom line in FIG. 3 is reached.

Figure 4A:
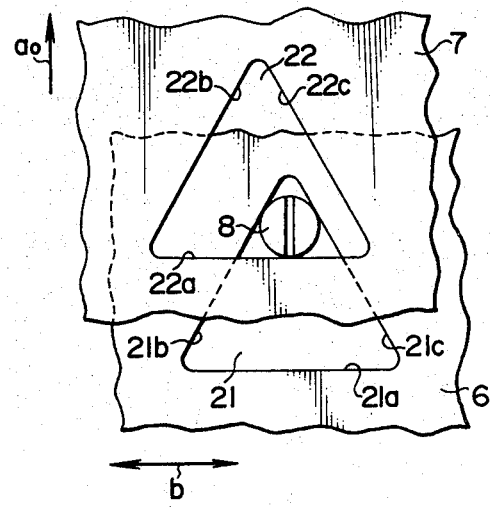
FIGS. 4(A) and (B) and FIGS. 5(A) and (B) are enlarged fragmentary views of the apparatus shown in FIG. 1.
Figure 4B:
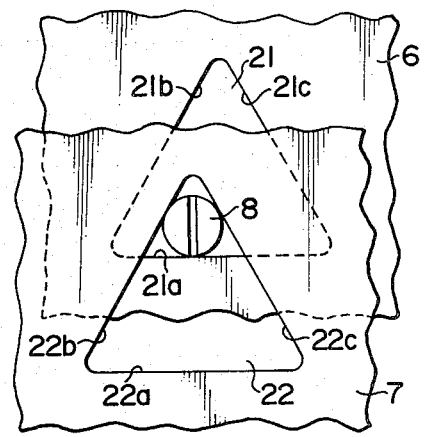

If the dioptry adjusting pin 8 is initially located at a right-hand position on the cam surface 22a, as shown in FIG. 4(A), the dioptry adjusting pin 8 is free from constraint by the cam surface 22a and becomes free to move within a common slot defined by both cam slots 21, 22. However, as the photographic positioning cam sleeve 7 moves angularly, the pin bears against both cam surfaces 22b and 22c of the cam slot 22 and is eventually moved thereby against the cam surface 21a of the cam slot 21 as shown in FIG. 4(B), where it is positioned by the three cam surfaces 22b, 22c and 21a to be maintained at its photographing position.

Figure 5A:
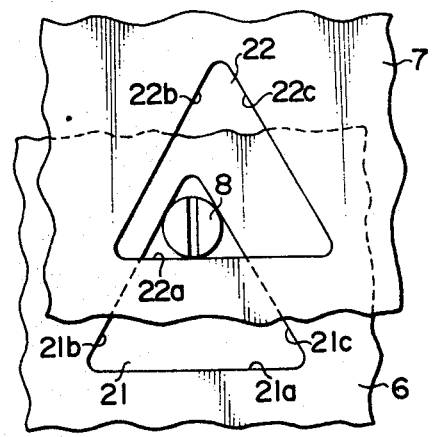
Figure 5B:
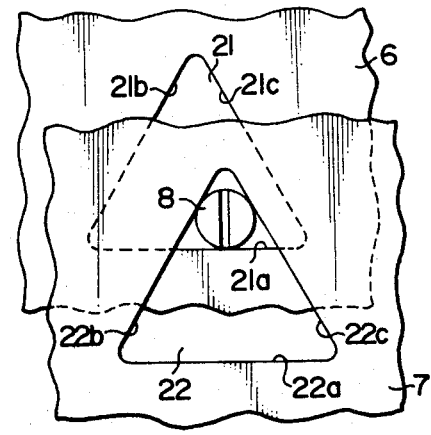

On the other hand, if the dioptry adjusting pin 8 is initially at a left-hand position on the cam surface 22a as shown in FIG. 5(A), it will be positioned and maintained at a photographing position defined by the cam surfaces 22b and 22c of the cam slot 22 and the cam surface 21a of the cam slot 21 as illustrated in FIG. 5(B), as the cam sleeve 7 is turned, in the same manner as if it were located at a right-hand position on the cam surface 22a.

It will be appreciated that the photographing position of the dioptry adjusting pin 8 in the direction of the optical axis thereof is determined by both cam surfaces 22b and 22c of the cam slot 22 formed in the photographic positioning cam sleeve 7, which is only capable of turning in the circumferential direction and incapable of moving parallel to the optical axis, and hence the photographing position remains fixed. Since the dioptry adjusting cam sleeve 6 in which the axial extending cam surface 21a is formed is only capable of moving axially, the circumferential position of the dioptry adjusting pin 8 is also maintained at a fixed point. It is to be understood that the eyepiece 3 presents a dioptry which is suitable for taking a picture at the photographing position of the dioptry adjusting pin 8. In this manner, the eyepiece 3 is positioned at a given photographing position as a photographing device is mounted.

An operation of the dioptry adjusting ring 9 in the photographing position only causes a sliding movement of the dioptry adjusting cam sleeve 6 with its cam surface 21 bearing against the dioptry adjusting pin 8, and does not cause a movement of the pin 8, thus avoiding any interference with operation of the photographing device.

When the photographing device is removed upon completion of a photographing operation, the arm 7b which is no longer constrained by the photographing device is allowed to rotate clockwise, as indicated by the arrow a in FIG. 3, to its original position shown in solid line, together with the photographic positioning cam sleeve 7, due to the resilience of the coiled spring 17. Specifically, the dioptry adjusting pin 8 is at first freely movable within a common slot defined by both cam slots 21 and 22 when the photographing device is removed, but is angularly driven by abutment against the cam surface 22a to be brought into abutment against the cam surface 21b or 21c, whereby it is caused to slide axially until it returns to the position shown in either FIG. 4(A) or FIG. 5(A) where it bears against both cam surfaces 21b and 21c. It is to be noted that, unless the dioptry adjusting ring 9 is operated during the photographing operation, this position is the same as the dioptry adjusted position of pin 8 before the photographing operation, which position is determined by the two cam surfaces 21b, 21c of the dioptry adjusting cam slot 21. Thus, a viewer can continue observation without readjusting the dioptry.

Figure 6:
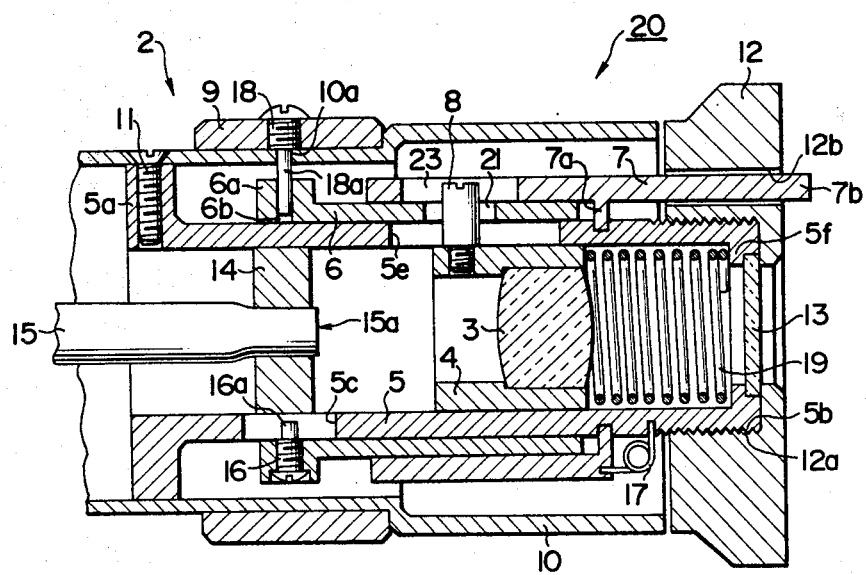
FIG. 6 is a longitudinal section of an apparatus for positioning the eyepiece of an endoscope according to another embodiment of the invention.

FIG. 6 shows an apparatus 20 for positioning the eyepiece according to another embodiment of the invention. The apparatus 20 is identical to the apparatus 1 shown in FIG. 1 except that the movable sleeve 4 is forwardly biased by a coiled compression spring 19 and that the cam slot 22 is replaced by a cam slot 23 having a different configuration. Accordingly, corresponding parts are designated by like reference characters and will not be described.

Figure 7A:
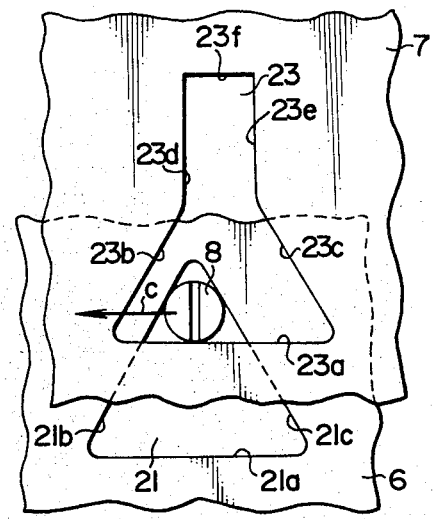
FIGS. 7(A) and (B) are enlarged fragmentary views of the apparatus shown in FIG. 6.

The coiled spring 19 is disposed between the radially inwardly extending ledge 5f of the fixed sleeve 5 and the movable sleeve 4 with its axis in alignment with the optical axis so as to avoid any interference with the optical path, thus maintaining the movable sleeve 4 forwardly biased. The cam slot 23 has the shape of a flask (see FIG. 7(A)) including an elongate notch defined by cam surfaces 23d-f and having a width slightly greater than the diameter of the dioptry adjusting pin 8 and extending from an apex which is located opposite to the axially extending cam surface 22a. Thus, the cam slot 23 includes the axially extending cam surface 23a, and the pair of cam surfaces 23b, 23c extending from the opposite ends of the cam surface 23a and defining the remaining two sides of the triangle, a pair of cam surfaces 23d, 23e extending from the upper ends of the cam surfaces 23b, 23c in a direction perpendicular to cam surface 23a, and a cam surface 23f which extends horizontally to join the upper ends of the cam surfaces 23d, 23e.

When the positioning apparatus 20 is used to observe the interior of a channel, the dioptry is adjusted in the same manner as in the apparatus 1 shown in FIG. 1, by turning the dioptry adjusting ring 9 in the circumferential direction to move the dioptry adjusting cam sleeve 6 along the optical axis. The dioptry adjusting pin 8 moves axially while being held between the cam surfaces 21b, 21c of the dioptry adjusting cam slot 21 and while bearing against the cam surface 23a of the photographic positioning cam slot 23. In this manner, the desired adjustment of the dioptry can be achieved, and a sharp image can be observed by a viewer.

Figure 7B:
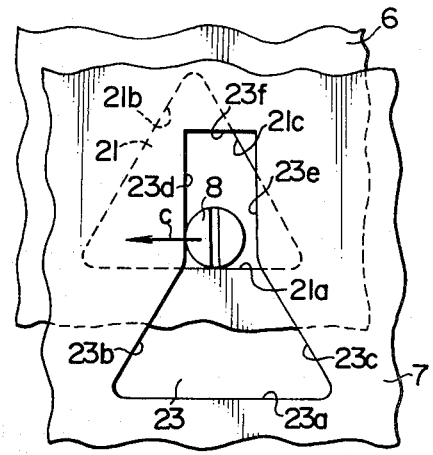

When taking a picture of the image being observed, the interlocking arm 7b is turned as a photographing device is mounted on the endoscope, thus rotating the photographic positioning cam sleeve 7, which is integral with the arm. The dioptry adjusting pin 8 which is located at its dioptry adjusted position shown in FIG. 7(A) moves forward along the cam surface 21b while bearing against the cam surface 23a during the initial phase, since it is urged in the direction of an arrow c by the coiled spring 19. When the pin 8 has moved forward and rotated to a position where it bears against the cam surface 21a, no further movement is possible. Subsequently, as the photographic positioning cam sleeve 7 further moves angularly from this position, the pin retracts axially along the cam surface 21a while bearing against the cam surface 23b until it has moved past the cam surface 23b to bear against the cam surface 23d, whereupon the photographic positioning cam sleeve 7 ceases to rotate and the pin comes to a stop in abutment against the cam surface 23d, due to resilience of the coiled spring 19 (see FIG. 7(B)). This position is maintained constant by the location of the cam surface 23d, independently of any dioptry adjusted position in the axial direction which it assumed prior to the mounting of the photographing device. A design is made such that a good picture of the object can be taken by the photographing device at this position of the eyepiece 3.

When the photographing device is dismounted upon completion of a photographing operation, the interlocking arm 7b is no longer constrained by the photographing device, and is returned to its normal position shown in solid line in FIG. 3 by the resilience of the coiled spring 17. The dioptry adjusting pin 8 now advances from the cam surfaces 23d onto the cam surfce 23b due to the resilience of the coiled spring 19 until it bears against the cam surface 23a, whereupon it is angularly driven by the cam surface 23a into abutment against the cam surface 21b where it is retracted axially, thus ultimately returning to the position shown in FIG. 7(A) where it bears against the both cam surfaces 21b and 21c. It will be noted that this position is the same as the dioptry adjusted position determined by the dioptry adjusting ring 9 which it assumed before the photographing operation. Consequently, the viewer is able to resume an observation without a re-adjustment of the dioptry.

In the embodiments shown in FIGS. 1 and 6, the apparatus positions the eyepiece by externally turning the interlocking arm 7b. Hence, the arrangement is subject to the constraint that a photographing device must be mounted on the eyepiece assembly 2 of the endoscope by a turning motion. Mounting a photographing device on the eyepiece assembly 2 by a turning motion is a cumbersome operation, and the photographing device must be provided with a special groove or projection which permits an engagement with the arm 7b. As a result, the arrangement requires the use of a dedicated camera device or attachment, preventing a universal use of the endoscope.

Additional disadvantages are that the arm 7b moves through an increased stroke as a photographing device is mounted, and that the arcuate slot 12b of an increased size must be formed in the eyepiece assembly 2 of the endoscope in order to secure the stroke of the arm 7b, preventing a water-proof construction of the eyepiece assembly 2.

Figure 8:
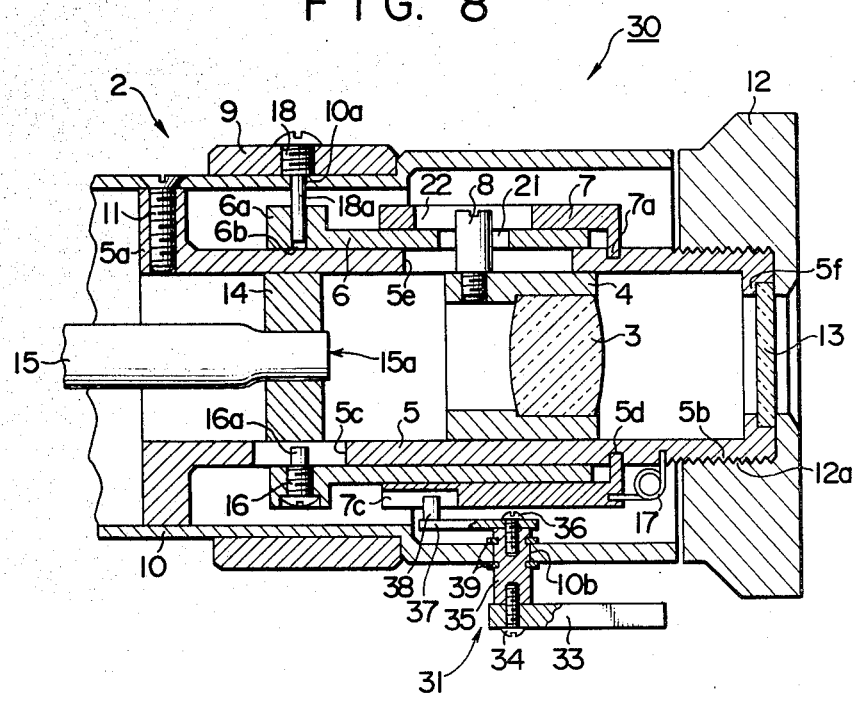
FIG. 8 is a longitudinal section of an apparatus for positioning the eyepiece of an endoscope according to a further embodiment of the invention.

FIG. 8 shows an eyepiece positioning apparatus according to a further embodiment of the invention which eliminates the above disadvantage by permitting a photographing device to be mounted on the eyepiece assembly 2 of the endoscope by a mere fitting engagement. The positioning apparatus 30 differs from the apparatus 1 shown in FIG. 1 in that an interlocking means 31 is substituted for the combination of the arm 7b and the arcuate slot 12b provided in the arrangement of FIG. 1 and is urged by a photographing device as it is mounted to cause an angular movement of the photographic positioning cam sleeve 7.

Figure 9:
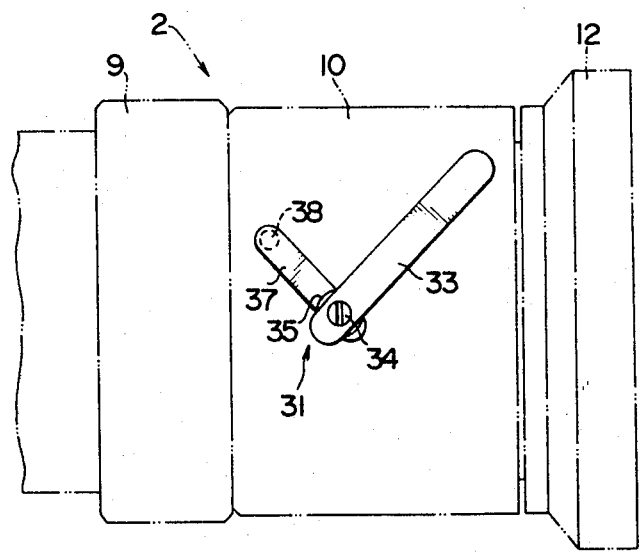
FIG. 9 is a fragmentary rear view of the apparatus shown in FIG. 8, illustrating the positional relationship between an interlocking rod and a follower rod.

The interlocking means 31 includes an interlocking rod 33 which is angularly driven as a photographing device is mounted, a rotary shaft 35 having one end of the rod 33 secured to its external end face by means of a set screw 34, a follower rod 37 having one end secured to the inner end face of the rotary shaft 35 by a set screw 36, and a pin 38 fixedly mounted on the free end of the follower rod 37. The rotary shaft 35 extends through a bearing hole 10b formed in the outer housing or frame 10 and is rotatably supported thereby. The shaft 35 is engaged by locking rings 39 which prevent the shaft from being disengaged from the bearing hole 10b. The interlocking rod 33 is exposed externally of the frame 10 while the follower rod 37 is disposed within the frame 10. The pin 38 extends into an elongate groove 7c formed in the external surface of a lower portion of the photographic positioning cam sleeve 7 at its front end. Since the cam sleeve 7 is angularly urged by the coiled spring 17, the interlocking rod 33 normally stays at rest with an angle of approximately 45° with respect to the optical axis, with its free end directed toward the frame 12, as shown in FIG. 9. The follower rod 37 is mounted so as to be substantially at right angles to the rod 33. When the rod 33 is angularly driven from the position about the rotary shaft 35 shown in FIGS. 8 and 9 to reach a position where it is substantially perpendicular to the optical axis, the photographic positioning cam sleeve 7 turns circumferentially against the resilience of the coiled spring 17.

Figure 10:
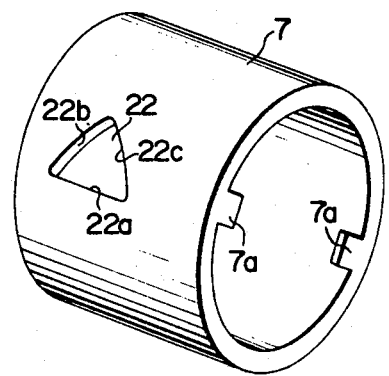
FIG. 10 is a perspective view of a photographic positioning cam sleeve used in the apparatus of FIG. 8.

As shown in FIG. 10, in this embodiment the interlocking arm is omitted from the rear end of the photographic positioning cam sleeve 7, and accordingly the frame 12 on which an eyepiece and photographing devices mounted is not formed with an arcuate slot.

Figure 11A:
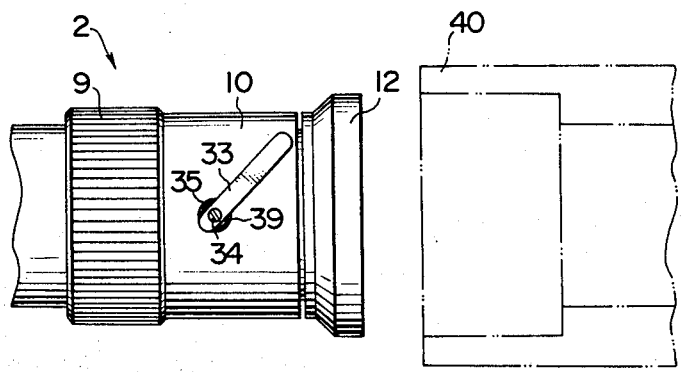
FIGS. 11(A) and (B) are rear views illustrating the manner of mounting a photographing device on the endoscope having the positioning apparatus shown in FIG. 8.
Figure 11B:
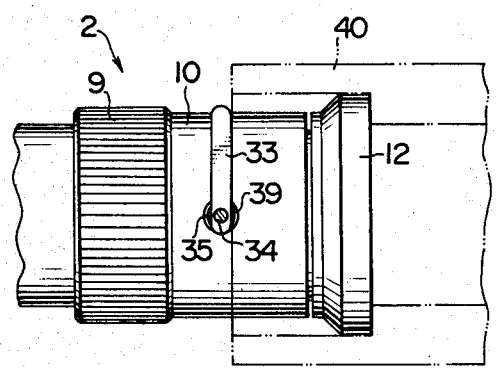

Briefly describing the operation of the positioning apparatus 30 when a photographing device is mounted on the endoscope, FIG. 11(A) shows an initial phase of fitting a photographing device 40 over the eyepiece assembly 2 of the endoscope. The front end face of the photographing device 4 bears against the free end of the interlocking rod 33, which is therefore rotated to a position substantially perpendicular to the optical axis, as illustrated in FIG. 11(B). As the rod 33 rotates, the follower rod 37 rotates counter-clockwise, whereby the pin 38 fixedly mounted on the rod 37 causes the photographic positioning cam sleeve 7 to turn circumferentially against the resilience of the coiled spring 17. The angular movement of the photographic positioning cam sleeve 7 is effective to move the dioptry adjusting pin 8, which is held between the cam surfaces 22b and 22c of the photographic positioning cam slot 22 and the cam surface 21a of the dioptry adjusting cam slot 21, to a photographing position determined by the cam surfaces 22b and 22c. Hence, the eyepiece 3 which is connected integrally with the dioptry adjusting pin 8 is positioned at a constant photographing position, permitting a photographing operation.

When the photographing device 40 is removed upon completion of the photographing operation, the interlocking rod 33 is no longer constrained by the photographing device 40, whereby the resilience of the coiled spring 17 causes rod 33 to be returned from the position shown in FIG. 11(B) to the original position shown in FIG. 11(A), together with the photographic positioning cam sleeve 7 and the follower rod 37. As the photographic positioning cam sleeve 7 returns to its original position, the dioptry adjusting pin returns to its dioptry adjusted position which it had prior to the photographing operation and where it bears against the both cam surfaces 21b, 21c of the dioptry adjusting cam slot 21 formed in the dioptry adjusting cam sleeve 6. Consequently, the eyepiece 3, being integral with the dioptry adjusting pin 8, returns to its dioptry adjusted position, permitting a viewer to continue observation without requiring a re-adjustment of the dioptry.

Figure 12:
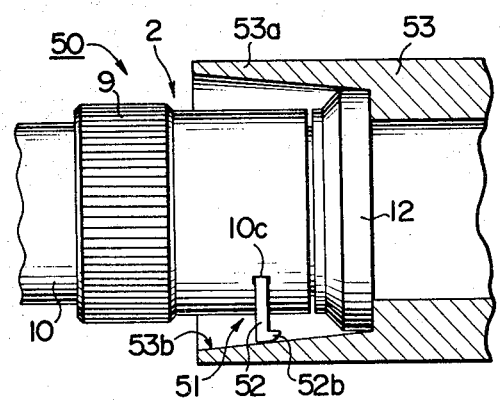
FIGS. 12 and 13 are a side elevation and a fragmentary cross section of an apparatus for positioning the eyepiece according to still another embodiment of the invention.
Figure 13:
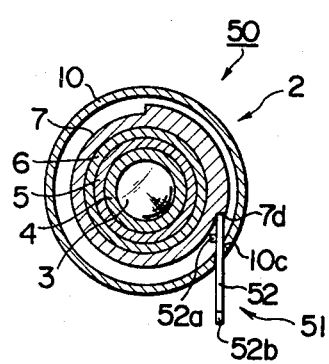

FIGS. 12 and 13 illustrate an eyepiece positioning apparatus according to an additional embodiment of the invention. The apparatus 50 shown includes interlocking means 51 which is substituted for the interlocking means 31 of FIG. 8 and formed by the interlocking rod 33 and the follower rod 37. The interlocking means 51 comprises an interlocking rod 52 which is mounted on the frame 10 so as to be slidable in a direction perpendicular to the optical axis, and a step 7d formed on part of the external wall of the photographic positioning cam sleeve 7 for engagement with the inner end of the rod 52.

Toward its inner end, the rod 52 is formed with a projection 52a which prevents withdrawal thereof, and its outer end is formed with a hook 52b. The rod 52 is disposed so that its inner end bears against the step 7d on the photographic positioning cam sleeve 7 while its outer end projects externally of the frame 10 by passing through a hole 10c formed therein in a right-hand, lower region thereof, as viewed in FIG. 13. The projection 52a prevents withdrawal of the rod 52 out of the frame 10. When the photographic positioning cam sleeve 7 is not angularly driven and assumes its normal position, the resilience of the coiled spring 17 (see FIGS. 1 and 8) causes the upper end face of the rod 52 to bear against the step 7d and to cause the projection 52a to bear against the sleeve 7 adjacent to the hole 10c, thus preventing rattling thereof.

A photographing device 53 has an opening 53a which is adapted to be fitted over the apparatus 50. The inner surface of the opening 53a is defined by a tapered surface 53b. When the device 53 is fitted over the apparatus 50, the hook 52b of the interlocking rod 52 is engaged by the tapered surface 53b and is raised upward or into the frame 50. Thereupon, the photographic positioning cam sleeve 7 is turned in the circumferential direction against the resilience of the coiled spring 17, whereby the eyepiece 3 is positioned in the same manner as illustrated above in connection with the apparatus 1 of FIG. 1.

When the photographing device 53 is removed, the cam sleeve 7 returns to its normal position due to the resilience of the spring 17, and hence the eyepiece 3 returns to its dioptry adjusted position which it had prior to the photographing operation. The rod 52 is depressed by the step 7d to return to its original position.

Figure 14:
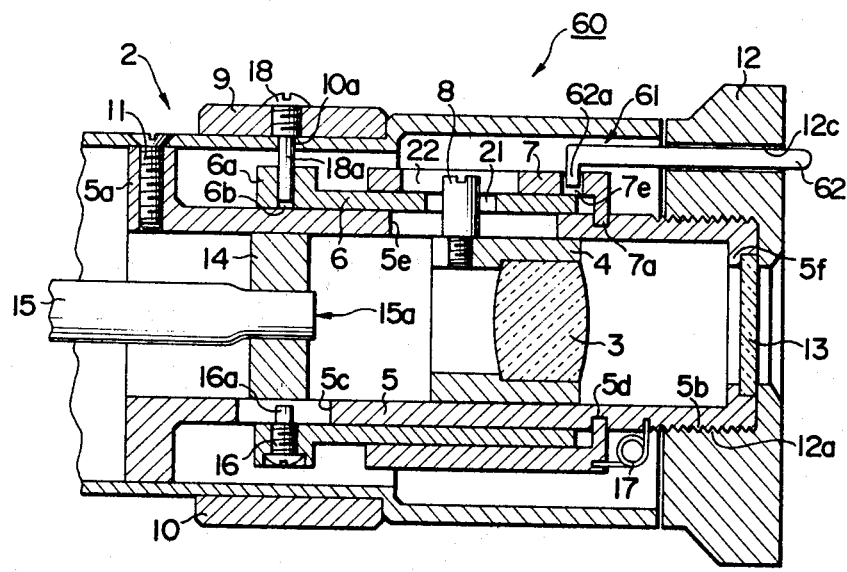
FIG. 14 is a longitudinal section of an apparatus for positioning the eyepiece according to a still further embodiment of the invention.

FIG. 14 shows an eyepiece positioning apparatus according to still another embodiment of the invention. The apparatus 60 shown is quite similar in arrangement to the apparatus 30 described above except that the interlocking means 31 of the apparatus 30 which includes the angularly movable rod 33 is replaced by interlocking means 61, which comprises an interlocking rod 62 disposed on the frame 12 so as to be slidable parallel to the optical axis, and a cam slot 7e (see FIG. 15) formed in the photographic positioning cam sleeve 7.

Figure 15:
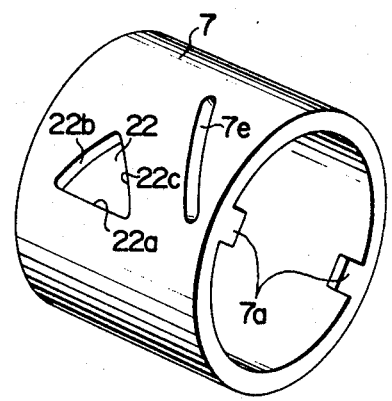
FIG. 15 is a perspective view of a photograph positioning cam sleeve used in the apparatus shown in FIG. 14.

The interlocking rod 62 is formed with a downwardly depending piece 62a on one end which is fitted into the cam slot 7e, which is formed at an angle with respect to the circumferential direction of the photographic positioning cam sleeve 7, as shown in FIG. 15. The other end or rear end of the rod 62 extends through an opening 12c formed in the frame and extending parallel to the optical axis, whereby the rear end of the rod projects rearwardly of the frame 12.

When a photographing device is mounted on the frame 12, the rod 62 is driven by one surface of the photographing device to move axially. The resulting movement of the rod 62 causes the cam sleeve 7 to turn in the circumferential direction against the resilience of the spring 17, through the cooperation between the depending piece 62a and the cam slot 7e. Consequently, the eyepiece 3 is positioned in the same manner as described above in connection with the apparatus 1 of FIG. 1. When the photographing device is dismounted, the resilience of the spring 17 returns the cam sleeve 7 to its original position as before, and hence the eyepiece 3 is returned to its dioptry adjusted position which it had prior to the photographing operation. The rod 62 is also returned to its original position.

Figure 16:
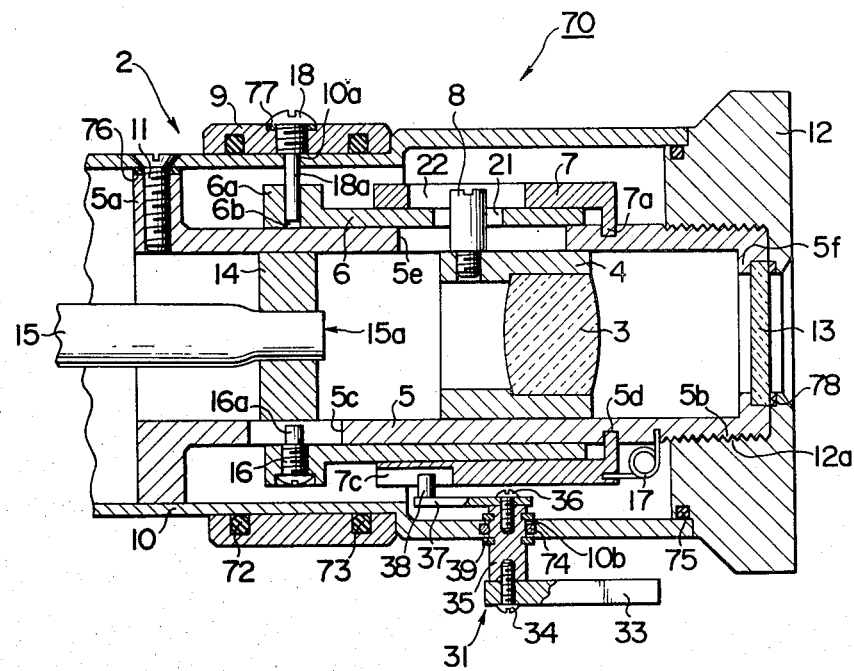
FIG. 16 is a longitudinal section of an apparatus for positioning the eyepiece according to an additional embodiment of the invention, illustrating a modification of the apparatus shown in FIG. 8 so as to make it a water-proof structure.

FIG. 16 shows an eyepiece positioning apparatus according to a still further embodiment of the invention in which the positioning apparatus 30 shown in FIG. 8 is modified into a water-proof construction. The apparatus 70 shown is constructed in the same manner as the apparatus 30 except that rubber rings 72–75 and rubber gaskets 76–78 are suitably located within the arrangement of the apparatus 30.

The rubber rings 72 and 73 are interposed between the frame 10 and the dioptry adjusting ring 9 on the opposite sides of the set screw 18. The rubber ring 74 is interposed between the frame 10 and the rotary shaft 35 of the interlocking rod 33, and the rubber ring 75 is interposed between the frame 10 and the frame 12. In this manner, these rubber rings prevent ingress of water or other liquids into the eyepiece assembly. The rubber gasket 76 is interposed between the frame 10 and the flange 5a of the fixed sleeve 5 so as to allow the passage of the set screw 11 therethrough. The rubber gasket 77 is disposed around the set screw 18 between the dioptry adjusting ring 9 and the set screw 18. The rubber gasket 78 is interposed between the cover glass 13 and the frame 12. In this manner, these rubber gaskets also serve preventing ingress of water or the like into the eyepiece assembly 2.

In this manner, the eyepiece assembly 2 is completely sealed against the ingress of water, and since the remainder of the endoscope is inherently constructed in a water-tight manner, the resulting endoscope can be cleaned after use by immersion into water, sterilizing liquid or detergent liquid.

It should be understood that the water-proof construction of the eyepiece assembly 2 shown in this embodiment is equally applicable to other apparatus 50 and 60 shown in FIGS. 12, 13 and 14, in addition to the apparatus 30 shown in FIG. 8.

It will be noted that the eyepiece positioning apparatus 30, 50, 60 or 70 shown in FIGS. 8, 12, 13, 14 or 16 is subject to the limitation that they are only usable with a photographing device or attachment with translates, as it is mounted, through a stroke which is just sufficient to move the eyepiece 3 to its photographing position, since the photographing device associated with these embodiments are mounted by axially moving it rather than angularly turning it and since there is a one-to-one correspondence between the stroke and the amount through which the photographic positioning sleeve 7 rotates.

Figure 17:
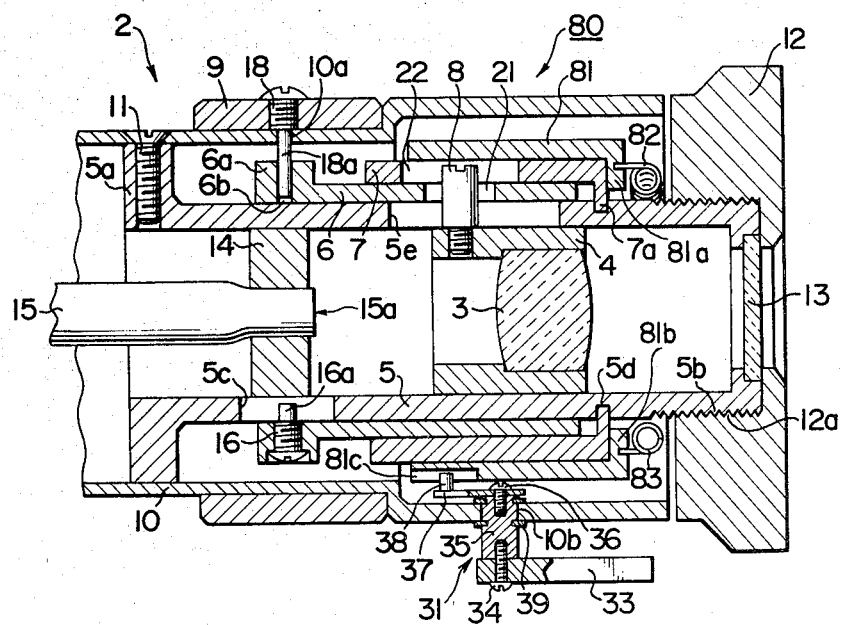
FIG. 17 is a longitudinal section of an apparatus for positioning the eyepiece according to still another embodiment of the invention.

This disadvantage is eliminated by an eyepiece positioning apparatus shown in FIG. 17 which represents another embodiment of the invention. In this instance, an apparatus similar to the apparatus 30 shown in FIG. 8 is provided with resilient means and a lost motion mechanism so that the eyepiece can always be positioned at a given photographing position irrespective of the stroke through which a photographing device is moved. The apparatus 80 shown includes a photographing sleeve 81 which is tightly fitted over the photographic positioning cam sleeve 7 so as to be rotatable about the optical axis. The sleeve 81 is in the form of a hollow cylinder having a pair of upper and lower pawls 81a, 81b (see FIG. 18) which extend radially inward from the rear end thereof at diametrically opposite positions. A coiled tension spring 82 which serves as a return spring is disposed between the upper pawl 81a and the fixed sleeve 5 while an interconnecting, coiled tension spring 83 is disposed between the lower pawl 81b and the photographic positioning cam sleeve 7. A circumferentially extending relief slot 81d is formed in the lower, right-hand portion of the sleeve 81 as viewed in FIG. 18, and cooperates with a detent pin 84 which is fixedly mounted on the cam sleeve 7 to permit an angular movement of the photographing sleeve 81 only in the circumferential direction. Upon the action of the coiled spring 83, one end of the slot 81d is engaged by the detent pin 84, whereby the cam sleeve 7 and the photographing sleeve 81 are connected together in an integral manner. Under the action of the coiled spring 82, the guide pin 16a normally bears against the side of the elongate guide slot 5c. Specifically, since the cam sleeve 7 and the photographing sleeve 81 are interconnected in an integral manner by the connecting spring 83, the resilience of the spring 82 causes the cam surface 22a of the cam slot 22 to bear against the dioptry adjusting pin 8, which in turn bears against the cam surfaces 21b, 21c of the cam slot 21 formed in the dioptry adjusting cam sleeve 6 carrying the guide pin 16a which is brought into abutment against the fixed sleeve 5, in the same manner as in the apparatus 1 shown in FIG. 1. An elongate groove 81c is formed in the external or lower surface of the photographing sleeve 81 at its front end and is engaged by the pin 38 which is fixedly mounted on the follower rod 37 of the interlocking means 31. In this manner, the photographing sleeve 81 is driven by the interlocking means 31 for angular movement.

Figure 19:
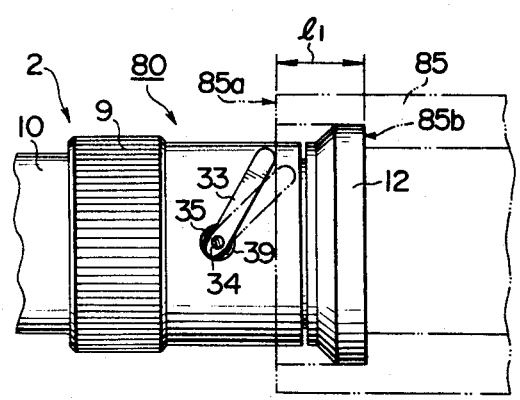
FIGS. 19 and 20 are rear views illustrating the manner of mounting a photographing device on the endoscope carrying the apparatus shown in FIG. 17.
Figure 20:
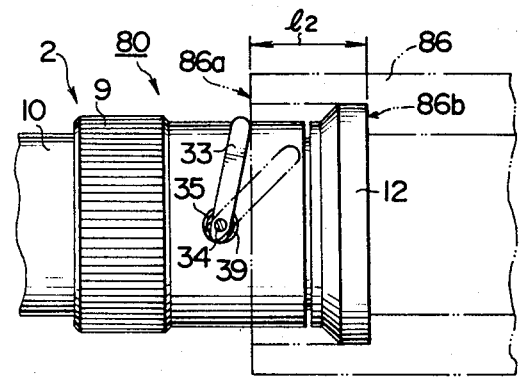
Figure 21:
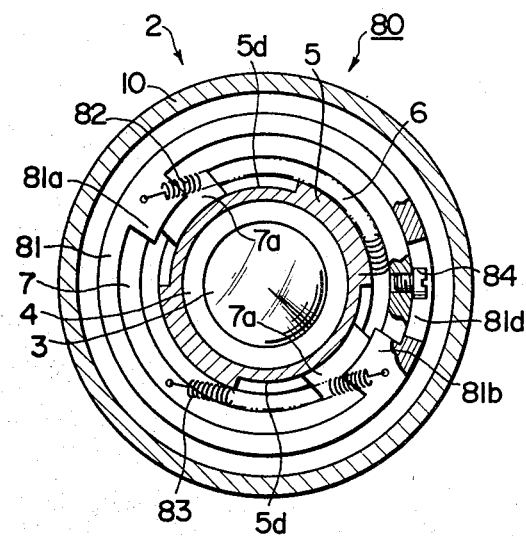
FIGS. 21 and 22 are enlarged cross sections of the apparatus shown in FIG. 17, illustrating different operative positions.

In use, when a photographing device 85 (see FIG. 19) having a relatively small distance $l_1$ between its opening end face 85a and its abutment surface 85b adapted to bear against the eyepiece assembly 2, is fitted over the eyepiece assembly 2, the free end of the interlocking rod 33 will be slightly rotated from its normal position shown in phantom line as it is driven by the end face 85a. On the other hand, when a photographing device 86 (see FIG. 20) having a relatively large distance $l_2$ between its opening end face 86a and its abutment surface 86b adapted to bear against the eyepiece assembly 2 is mounted, the interlocking rod 33 will be rotated through a larger angle from its normal position, again shown in phantom line.

Figure 18:
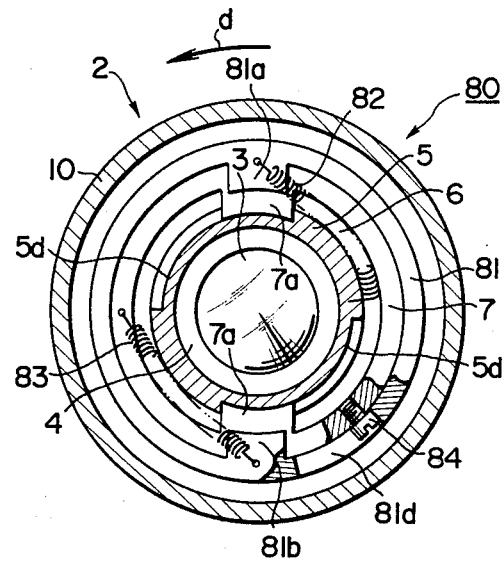
FIG. 18 is a fragmentary cross section of the apparatus shown in FIG. 17.

In response to such rotation of the interlocking rod 33, photographing sleeve 81 will be initially driven by means of the engagement between the pin 38 on the follower rod 37 and the groove 81c to rotate in a direction indicated by arrow d from its position shown in FIG. 18 against the resilience of the return spring 82, the photographic positioning cam sleeve 7 rotating with it.

As the cam sleeve 7 rotates, the dioptry adjusting pin 8 is positioned by being held between the cam surfaces 22b, 22c of the cam slot 22 and the cam surface 21a of the dioptry adjusting cam slot 21 in the same manner as mentioned above in connection with FIG. 1, whereby the eyepiece 3 is brought to a given photographing position.

Figure 22:
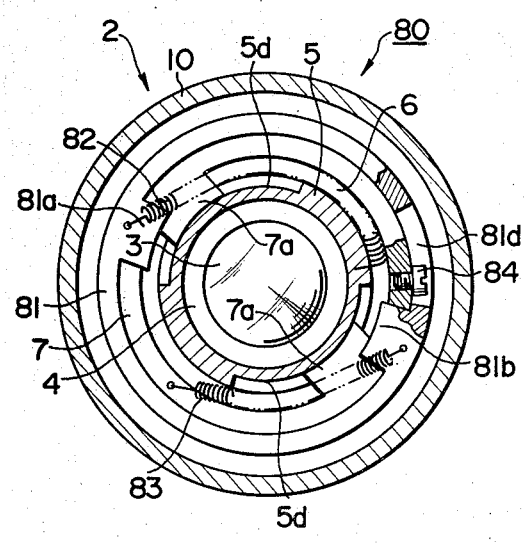

As the photographic positioning cam sleeve 7 rotates integrally with the photographing sleeve 81, the cam surfaces 22b, 22c come into abutment against the dioptry adjusting pin 8, whereby further rotation is prevented. Subsequently, the photographing sleeve 81 continues to rotate against the resilience of the springs 82, 83 in response to the rotation of the interlocking rod 33 which results from a further axial translation of photographing device 85 or 86. Ultimately, the detent pin 84 begins to be spaced from the end face of the relief slot 81d as shown in FIG. 22, so that the photographing sleeve 81 comes to a stop after rotating through a small angular stroke for the photographing device 85 and through a larger angular stroke for the photographing device 86 from the angular position where the photographic positioning cam sleeve 7 has ceased to rotate, against the resilience of the springs 82, 83. When the photographing sleeve comes to a stop in this manner, the resilience of the springs 82, 83 acts on the end face 85a or 86a of the photographing device 85 or 86.

When either photographing device 85 or 86 is dismounted upon completion of a photographing operation, the interlocking rod 33 is no longer constrained by such device, and hence initially rotates together with the photographing sleeve 81 under the resilience of the springs 82, 83 until the detent pin 84 bears against the end face of the slot 81d. Thereafter, both sleeves 81 and 7 are connected together, and continue to rotate under the resilience of the spring 82. Consequently, the dioptry adjusting pin 8 is held between the cam surfaces 21b, 21c of the cam slot 21 and the cam surface 22a of the cam slot 22, and the eyepiece 3 returns to its dioptry adjusted position which it had prior to the photographing operation.

In this manner, in the positioning apparatus 80 of this embodiment, a lost motion mechanism comprising interconnecting spring 83, detent pin 84 and relief slot 81d is formed between the photographing sleeve 81 and the photographic positioning sleeve 7, so that it is always assured that the eyepiece 3 be positioned at a given photographing position independently from the stroke or the configuration of the end face of the photographing device.

Figure 23:
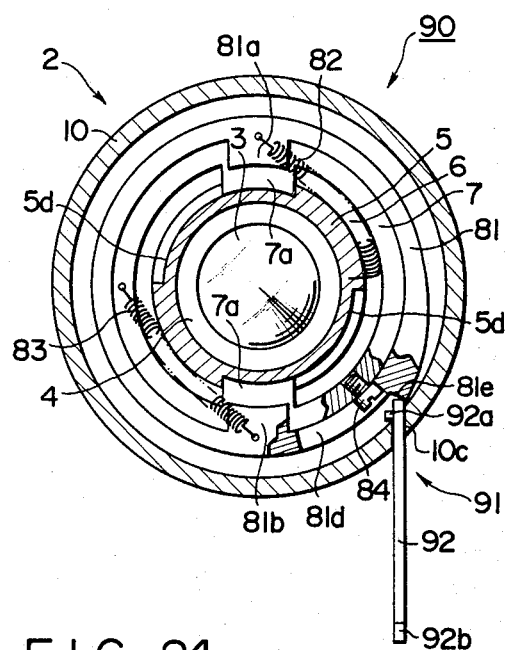
FIGS. 23 and 24 are an enlarged cross section and a side elevation of an apparatus for positioning the eyepiece according to a still further embodiment of the invention.

FIG. 23 shows yet another embodiment of the invention. An eyepiece positioning apparatus 90 of this embodiment has substituted interlocking means 91 for the interlocking means 31 used in the apparatus 80 of FIG. 17 and formed by the interlocking rod 33 and the follower rod 37. The interlocking means 91 is constructed generally in the same manner as that used in the apparatus 50 of FIGS. 12 and 13, and comprises an interlocking rod 92 which is mounted on the frame 10 so as to be slidable in a direction perpendicular to the optical axis, and a step 81e formed on part of the external surface of the photographing cam sleeve 81 for engagement with the inner end of the interlocking rod 92.

Toward its inner end, the rod 92 is formed with a locking projection 92a, and its outer end is formed with a hook 92b. The rod 92 is disposed so as to extend through a hole 10c formed in the frame 10 in its right-hand lower wall, as viewed in FIG. 23, so that its inner end bears against the step 81 on the photographing sleeve 81, with its outer end projecting externally of the frame 10. When the sleeve 81 is not angularly driven and assumes its normal position, the inner end of the rod 92 is maintained in abutment against the step 81 while the locking projection 92a bears against the frame 10 adjacent to the hole 10c to prevent rattling thereof.

Figure 24:
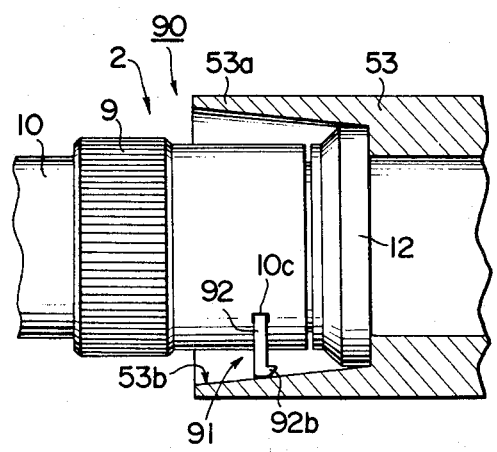

When a photographing device 53 having an opening 53a, the inner surface of which is formed as a tapered surface 53b, is fitted over the eyepiece assembly 2 which is provided with the apparatus 90, as shown in FIG. 24, the hook 92b of the interlocking rod 92 is engaged and raised by the tapered surface 53b. Thereupon, the photographing sleeve 81 is turned in the circumferential direction, thus positioning the eyepiece 3 in the same manner as with the apparatus 80 shown in FIG. 17. Since a lost motion mechanism comprising connecting spring 83, detent pin 84 and relief slot 81d is disposed between the photographing sleeve 81 and the photographic positioning sleeve 7, the eyepiece 3 can be located at a given photographing position independently of the stroke through which the photographing device 53 translates and of the angle of the tapered surface 53b.

When the photographing device 53 is removed, the sleeves 81, 7 return to their normal position due to the resilience of the springs 82, 83 in the same manner as in the apparatus 80, and consequently the eyepiece 3 resumes the dioptry adjusted position which it had prior to the photographing operation. Finally, the interlocking rod 92 falls, its withdrawal being prevented by the locking projection 92a until it comes to rest.

Figure 25:
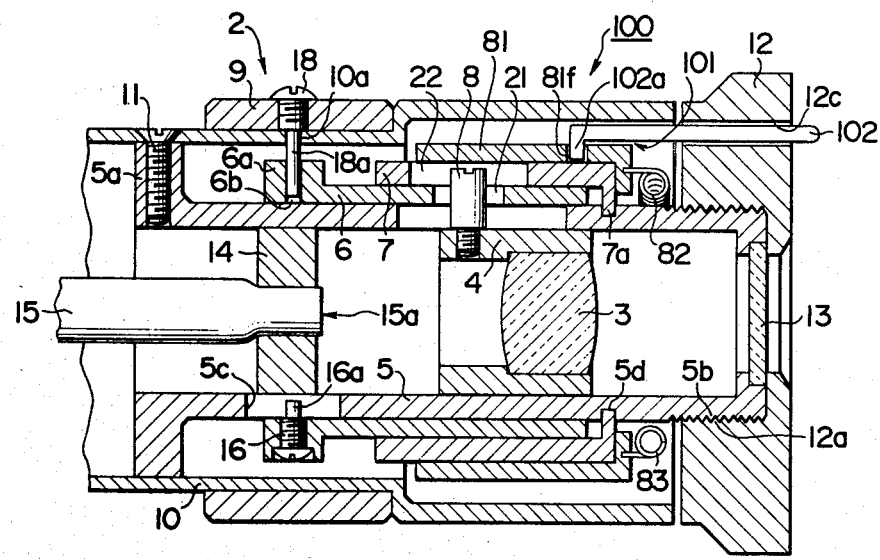
FIG. 25 is a longitudinal section of an apparatus for positioning the eyepiece according to yet another embodiment of the invention.

FIG. 25 shows yet another embodiment of the invention. The apparatus 100 shown is similar to the apparatus 80 shown in FIG. 17, but the interlocking means 31 of the apparatus 80 is replaced by interlocking means 101 similar to that used in the apparatus 60 of FIG. 14 and which comprises an interlocking rod 102 disposed so as to be slidable parallel to the optical axis, and a cam slot 81f formed in the photographing sleeve 81.

Figure 26:
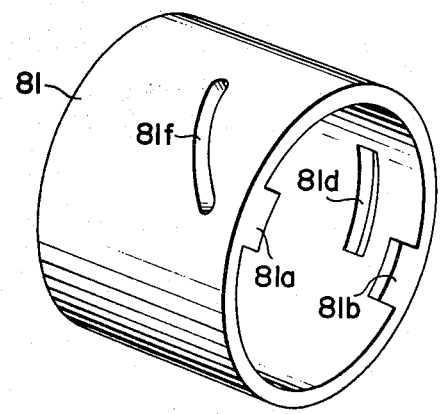
FIG. 26 is a perspective view of a photographing sleeve used in the apparatus shown in FIG. 25.

The rod 102 is slidably disposed within a through-opening 12c extending in a direction parallel to the optical axis and formed in the frame 12. At its inner end, the rod is formed with a downwardly depending piece 102a, which is fitted into the cam slot 81f formed in the photographing sleeve 81 at an angle with respect to the circumferential direction thereof, as shown in FIG. 26. The rear end of the rod 102 projects rearwardly of the frame 12.

When a photographing device is mounted on the frame 12 provided with the apparatus 100, the rod 102 moves parallel to the optical axis as it is driven by one surface of the photographing device. The movement of the rod 102 causes the depending piece 102a to rotate the photographing sleeve 81 in the circumferential direction against the resilience of the spring 82. Consequently, the photographic positioning sleeve 7 which is resiliently coupled therewith through the spring 83 also rotates in the circumferential direction, thus positioning the eyepiece 3 in the same manner as occurs in the apparatus 80 of FIG. 17.

When the photographing device is dismounted upon completion of a photographing operation, the sleeves 81, 7 return to their normal positions due to the resilience of the springs 82, 83 as before, whereby the eyepiece 3 resumes the dioptry adjusted position which it had prior to the photographing operation.

It should be understood that the apparatus 80, 90 and 100 shown in FIGS. 17, 23 and 25 may be modified to provide an eyepiece assembly 2 of a water-proof construction, by using sealing members such as rubber rings and rubber gaskets in a manner illustrated in FIG. 16.

FIGS. 27 to 31 illustrate several different forms of the dioptry adjusting cam slot and the photographic positioning cam slot which may be used in the apparatus of the invention.

Figure 27:
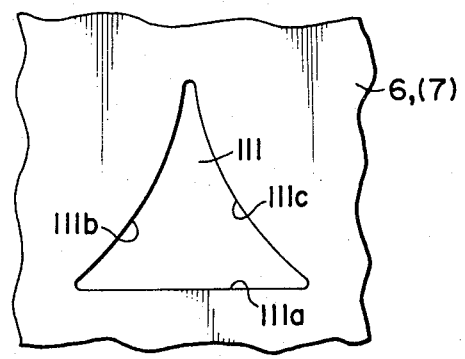
FIGS. 27 to 31 are plan views illustrating several forms of the dioptry adjusting and the photographic positioning cam slot which are preferred for use in the apparatus of the invention.
Figure 28:
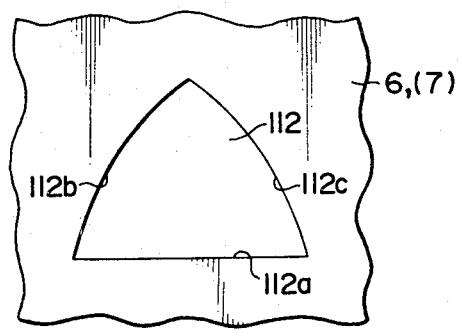
Figure 29:
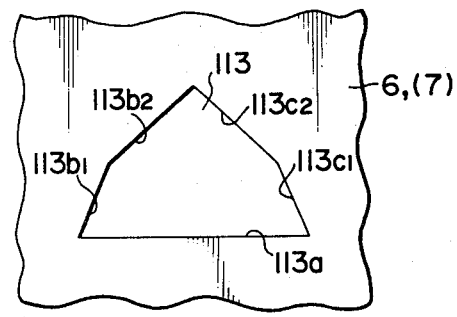
Figure 30:
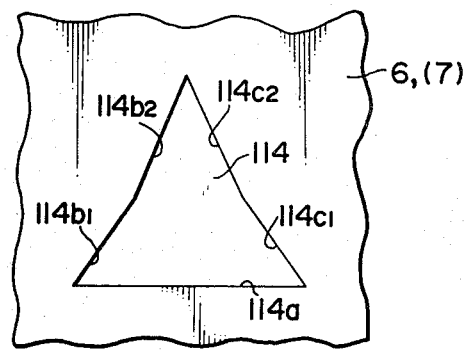
Figure 31:
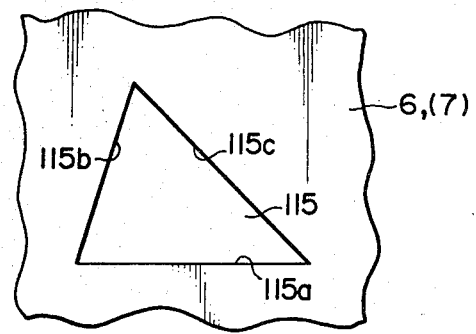

FIGS. 27 and 28 illustrate cam slots 111, 112 having curved or arcuate cam surfaces 111b, 111c or 112b, 112c even though cam surfaces 111a, 112a are rectilinear, extending parallel to the optical axis. FIGS. 29 and 30 illustrate cam slots 113, 114 of polygonal form including a plurality of cam surfaces 113b1, 113b2, 113c1, 113c2, 114b1, 114b2, 114c1, 114c2 except for axial extending cam surfaces 113a, 114a. Finally, FIG. 31 illustrates a cam slot 115 in which an apex of the triangle which is located opposite to an axially extending cam surface 115a is displaced laterally to provide two remaining cam surfaces 115b, 115c of different lengths or inclinations.

What is claimed is:

1. An eyepiece assembly for an endoscope, comprising:
   (A) a lens sleeve supporting a lens of said eyepiece assembly and being slidably mounted for translational movement along an optical axis of said lens;
   (B) a photographic positioning cam sleeve mounted for rotational movement about said axis, said photographic positioning cam sleeve having a photographic positioning cam slot formed therein;
   (C) a dioptry adjusting cam sleeve mounted for translational movement along said axis, said dioptry adjusting cam sleeve having a dioptry adjusting cam slot formed therein; and
   (D) a dioptry adjusting pin connected to said lens sleeve and extending through both of said cam slots, said pin cooperating with said cam slots in such a manner that:
      (1) said cam slot in said photographic positioning cam sleeve positions said pin, and therefore said lens, at a predetermined axially position, corresponding to a photographing position, when said photographic positioning cam sleeve is in a first angular position; and
      (2) said cam slot in said dioptry adjusting cam sleeve positions said pin, and therefore said lens, at an axial position determined by the axial position of said dioptry adjusting cam sleeve when said photographic positioning cam sleeve is in a second angular position, different from said first angular position.

2. An eyepiece assembly according to claim 1, further including manually adjustable means for axially translating said dioptry adjusting cam sleeve between first and second axial positions such that the axial location of said lens may be adjusted over a predetermined range when said photographic positioning cam sleeve is in said second angular position.

3. An eyepiece assembly according to claim 2, wherein said predetermined axial position is located within said predetermined range.

4. An eyepiece assembly according to any one of claims 1 or 3, wherein said photographic positioning cam sleeve is rotatable only between said first and second angular positions and further including means for biasing said photographic positioning cam sleeve into said second angular position.

5. An eyepiece assembly according to claim 4, further including means for rotating said photographic positioning cam sleeve into said first angular position in response to the mounting of a camera on said eyepiece assembly.

6. An eyepiece assembly according to claim 5, wherein said means for rotating comprises an arm extending from said photographic positioning cam sleeve in a direction parallel to said optical axis, said arm being integral with said photographic positioning cam sleeve so that it will rotate said photographic positioning cam sleeve when a camera is rotationally mounted on said eyepiece assembly and contacts said arm.

7. An eyepiece assembly according to claim 5, wherein said eyepiece assembly further includes an outer housing and wherein said means for rotating comprises an arm projecting outside said housing and being slidably mounted for movement in a direction parallel to said optical axis, an additional cam slot formed in said photographic positioning cam sleeve, said arm having an extension which engages said additional cam slot and cooperates with said additional cam slot in such a manner that said photographic positioning cam sleeve is rotated in response to the axial movement of said arm.

8. An eyepiece assembly according to claim 5, wherein said means for rotating comprises:
  (A) a photographing sleeve coaxial with said graphic positioning cam sleeve;
  (B) means for rotating said photographing sleeve when a camera is mounted on said eyepiece assembly; and
  (C) means for resiliently interconnecting said photographing and photographic positioning cam sleeves in such a manner that:
    (1) said photographic positioning cam sleeve is rotated with said photographing sleeve into said first angular position when said photographing sleeve is rotated through a predetermined angle; and
    (2) said photographing sleeve rotates independently of said photographic positioning cam sleeve when said photographing sleeve is rotated beyond said predetermined angle.

9. An eyepiece assembly according to claim 8, wherein said resiliently interconnecting means is a spring connected between said photographing and said photographic positioning cam sleeves.

10. An eyepiece assembly according to claim 1 in which said photographic positioning cam slot and said dioptry adjusting cam slot are each defined by a respective set of at least three cam surfaces, each said set including a cam surface which extends parallel to said optical axis.

11. An eyepiece assembly according to claim 10, in which said photographic positioning cam slot and dioptry adjusting cam slot are each triangular in configuration, said dioptry adjusting pin abutting concurrently against the two cam surfaces of said photographic positioning cam slot that are not parallel to said optical axis when said photographic positioning cam sleeve is in said first angular position so as to place said lens in said photographing position, and said dioptry adjusting pin abutting concurrently against the two cam surfaces of said dioptry adjusting cam slot that are not parallel to said optical axis when said photographic positioning cam sleeve is in said second angular position so as to place said lens in said axial position determined by the axial position of said dioptry adjusting cam sleeve.

12. An eyepiece assembly according to claim 1, in which said photographic positioning cam slot is defined by a plurality of cam surfaces, said plurality of cam surfaces including a circumferentially extending cam surface extending about a portion of the circumference of said photographic positioning cam sleeve, and said assembly further comprising resilient means that biases said lens sleeve in a direction which brings said dioptry adjusting pin into abutment against said circumferential cam surface to position said lens at said photographing position when said photographic positioning cam sleeve is in said first position.

13. An eyepiece assembly according to claim 5, in which said eyepiece assembly includes an outer housing and in which said means for rotating comprises in interlocking rod disposed for angular movement responsive to a camera being axially mounted on said eyepiece assembly, a rotary shaft having one end fixed to one end of said interlocking rod, said shaft passing through an opening formed in said outer housing, a follower rod having one end fixedly mounted on a second end of said rotary shaft, and a pin fixedly mounted on a second end of said follower rod, and said photographic positioning cam sleeve having an elongate groove formed therein and engaging said pin.

14. An eyepiece assembly according to claim 5, in which said eyepiece assembly includes an outer housing and wherein said means for rotating comprises an interlocking rod disposed to be slidable in a direction perpendicular to said optical axis and having an outer end projecting outside said outer housing, and in which said photographic positioning cam sleeve has a step formed therein which engages the inner end of said interlocking rod.

15. An eyepiece assembly according to claim 5, in which said eyepiece assembly includes an outer housing and wherein said means for rotating comprises an interlocking rod disposed to be slidable parallel to said optical axis, said interlocking rod having one end which projects outside said housing and having a piece extending from its other end for engaging said photographic positioning cam sleeve, and said photographic positioning cam sleeve having an additional cam slot formed therein which receives said piece which extends from said other end of said interlocking rod, said additional cam slot having a shape which will cause said photographic positioning cam sleeve to rotate in response to axial movement of said interlocking rod.

16. An eyepiece assembly according to claim 8, in which said eyepiece assembly includes an outer housing and wherein said means for rotating comprises an interlocking rod disposed for angular movement responsive to a camera being axially mounted on said eyepiece assembly, a rotary shaft having one end fixed to one end of said interlocking rod, said shaft passing through an opening formed in said outer housing, a follower rod fixedly mounted on a second end of said rotary shaft, and a pin fixedly mounted on a second end of said follower rod, and said photographing sleeve having an elongate groove formed therein and engaging said pin.

17. An eyepiece assembly according to claim 8, in which said eyepiece assembly includes an outer housing and wherein said means for rotating comprises an interlocking rod disposed to be slidable in a direction perpendicular to said optical axis and having an outer end which projects outside said housing, and in which said photographing sleeve has a step formed therein which engages the inner end of said interlocking rod.

18. An eyepiece assembly according to claim 8, in which said eyepiece assembly includes an outer housing and wherein said means for rotating comprising an interlocking rod disposed to be slidable parallel to said optical axis, said interlocking rod having one end which projects from said housing and having a piece extending from its other end for engaging said photographing sleeve, and said photographing sleeve having an elongated groove fromed therein which receives said piece extending from said other end of said interlocking rod, said elongated groove having a shape which causes said photographing sleeve to rotate in response to the sliding movement of said interlocking rod.

19. An eyepiece assembly according to any one of claims 2 or 3, in which said dioptry adjusting cam sleeve has an additional cam slot formed therein at an angle with respect to said optical axis; and wherein said manually adjusting means comprises a dioptry adjusting ring having a guide pin which is receiving in said additional cam slot, said dioptry adjusting cam sleeve being movable in a direction parallel to said optical axis in response to an angular movement of said dioptry adjusting ring in a circumferential direction.

20. An eyepiece assembly according to claim 1, said eyepiece assembly having a water-proof construction including seal members comprising rubber rings and rubber gaskets.

* * * * *